United States Patent

Hazlett

[11] Patent Number: 6,111,929
[45] Date of Patent: Aug. 29, 2000

[54] SCANNING X-RAY FLUORESCENCE ANALYZER

[75] Inventor: Thomas Hazlett, Cambridge, Mass.

[73] Assignee: XRF Corporation, Somerville, Mass.

[21] Appl. No.: 08/818,758

[22] Filed: Mar. 14, 1997

[51] Int. Cl.⁷ .............................................. G01N 23/223
[52] U.S. Cl. ........................................ 378/45; 378/210
[58] Field of Search ........................................ 378/45–49

[56] References Cited

U.S. PATENT DOCUMENTS

4,698,832  10/1987  Kuusi .......................................... 378/45
5,274,688  12/1993  Grodzins .................................... 378/45

Primary Examiner—Craig E. Church

[57] ABSTRACT

Disclosed is a scanning x-ray fluorescence spectrometer for measuring accurately the content of a randomly distributed element contained in a sample. Said device comprising a linear excitation source of radioactive material in a holder which produces a beam of ionizing radiation capable of exciting the emission of primary x-rays of the said element from said sample. The sample is mechanically drawn through said beam in a direction perpendicular to the axis of said source, thus exposing the entire sample to a uniform radiation flux. A linear radiation detector is positioned on a plane parallel to said sample and said source, positioned such that its sensitive area faces said sample at the point where the most intense portion of said beam passes through said sample, thus achieving a uniform collection of x-rays from the sample. A personal computer provides calibration, motor control and data analysis capability including an algorithm to convert nuclear data into an accurate reading of the concentration of the element in the sample.

8 Claims, 7 Drawing Sheets

SCANNING X-RAY FLUORESCENCE ANALYZER

FIELD OF THE INVENTION

This invention relates to a scanning x-ray fluorescence analyzer capable of measuring the concentration of selected elements randomly distributed in the medium used to collect the sample. The present invention allows the construction of a portable spectroscopy system capable of laboratory quality analysis.

BACKGROUND OF THE INVENTION

X-ray fluorescence spectroscopy permits measurement of the atomic composition of materials by observing the radiation emitted by a material when it is excited with a source of high energy photons such as x-rays or gamma rays. X-rays result when an electron is knocked out of its orbit around the nucleus of an atom by a photon from the source. When this occurs, an electron from an outer shell of the atom will fall into the shell of the missing electron. The excess energy in this interaction is expended as an x-ray photon. Since each element has a different and identifiable x-ray signature, the elemental composition of a sample can be identified.

Typically, x-ray fluorescence spectrometers include a source of radiation and a detector. The detector emits electrical impulses that are proportional to the energy of the photons being emitted by the sample. The impulses are amplified and pulses are counted from discrete portions of the sample's spectrum where x-rays emitted by the element under investigation can be found. The data is treated to isolate the x-rays being measured from other nuclear events and electronic noise with the aid of a computer.

Low-level lead poisoning is widespread among American children, afflicting as many as 3,000,000 children under age six. Lead poisoning causes intelligence quotient deficiencies, learning disabilities, hyperactivity and behavioral problems. Children can become poisoned through oral contact with the paint or through ingestion of dust containing lead paint. Upon detection of lead-based paint, the abatement process requires evacuation of the unit and removal or encapsulation of lead paint. A proper cleanup after abatement is essential since the residual dust is highly toxic. Post-abatement inspection is required prior to re-occupancy. Typically, a damp paper wipe is used to collect dust samples from the abatement site. The samples are then sent to accredited laboratories to measure their lead content.

The detection of lead-in-paint by x-ray fluorescence spectroscopy (XRF) has become the preferred method in the abatement industry because it is accurate and non-destructive. To measure lead in paint films the technician uses a portable spectrometer that has a source of gamma radiation such as cobalt 57 or cadmium 109, to irradiate the surface being analyzed, and a semiconductor detector, or a scintillation crystal coupled to a photomultiplier as the radiation detector. The technician simply holds the device against the surface for a measured amount of time and a reading is obtained. Unskilled operators can use these machines effectively. Most difficulties encountered with these devices occur when the underlying wall or molding presents an unusual backscatter spectrum, or the overlying non-lead paint layer thickness becomes great enough to cause attenuation of the underlying lead layers.

Conventional x-ray fluorescence spectrometers can produce quantitative results if either of two conditions are met: the sample is inherently uniform in analyte concentration, or the sample can be prepared such that its volume falls within the linear area of the particular spectrometers field of view. Randomly distributed analyte such as that found in dust wipe or air filter samples cannot usually be quantified without careful sample preparation. X-ray fluorescence spectrometers are inherently non-destructive, and can be made portable, repeatable, quantitative and capable of producing a hard copy result that can be validated.

It is an object of this invention to make possible the construction of a portable automatic x-ray fluorescence spectroscopy system capable of analyzing non-uniform samples of metallic elements, particularly lead in the microgram range, that are contained in or on the medium used to collect the metallic elements.

SUMMARY OF THE INVENTION

In aspects, this invention relates to an x-ray fluorescence analyzer that includes a linear excitation source of radiation, a linear detector, a transmitted radiation trap and a motor driven mechanism to move a sample through the device, built in a compact, portable instrument that is capable of reliably analyzing and quantifying microgram concentrations of metallic elements, particularly lead, that is contained in soil or other aggregates, or on a sample medium such as a post abatement dust wipe or an air sampling filter.

In one aspect this invention relates to a structure containing a line source of radiation, and a fluorescence source constructed from an element that when excited by the line source emits x-rays in a useful energy range. The fluorescence source is equal in length to the line source and positioned parallel to the line source. The sources are contained in a holder that produces a collimated beam of radiation consisting of x-ray and gamma radiation. The beam of radiation is uniform in intensity along the axis of the source assembly and is capable of uniformly irradiating a flat specimen that travels at constant speed through the beam in a direction that is perpendicular to the axis of the source. The source assembly is used in conjunction with a detector with an active length that is equal in length to the line source and is uniform in sensitivity along its length. Preferably in various embodiments, the absolute length of the source/detector assembly is greater than the width of the specimen under test. The sensor is constructed such that the axis of the line source lies parallel to the sample plain. The source assembly is positioned such that the beam it produces irradiates the portion of the sample that lies closest to the detector. The detector's active face lies parallel to the sample. The distance from sample to detector is the closest distance at which they can be positioned without allowing direct radiation from the source to hit the detector.

Another aspect of the invention relates to a one dimensional scan system that allows real time control over the scan increment and acquisition time to compensate for source decay.

Another aspect of the invention features a unique transmitted radiation trap. The trap is constructed from 1 mm thick tin plates mounted radially about the axis of the line source. The wall to which the radiation trap is attached, is constructed from a 180 degree section of 1 2" dia.×6" aluminum tubing. Photons from the source that interact between the plates will scatter or generate x-rays. In both cases the resulting photons are lower in energy and have no direct line of sight to the detector thus limiting the contribution of backscatter to the signal.

In another aspect of the invention the source assembly, detector and radiation trap are mounted in a high density enclosure that acts as a radiation safety shield. A graded shield lines all surfaces of the enclosure exposed to the detector. In preferred embodiments the graded shield is composed of sintered tungsten lined with tin. Tin is used because it will efficiently absorb fluorescence from the tungsten collimator walls that would interfere with the desired lead signal, while emitting x-rays at an energy separate from the photons being measured.

In another aspect of the invention the specimen is loaded into a holder fabricated from mylar or other low density material. The mylar holder travels through the sensor assembly between the source and transmitted radiation trap where it is irradiated and the resulting impulses are read by the detector.

Various embodiments of the invention herein described include one or more preamplifiers to convert charges from the detectors into voltage pulses, additional amplification to differentiate, integrate and further increase the voltage of said pulses, two or more windowing circuits to allow counting of photons from discrete energy ranges of the spectrum, and a computer loaded with a program to convert raw nuclear count data into a weight measurement of the element being measured. The computer program also includes routines to control sample manipulation, to calculate source strength, and to provide hard copy documentation of results.

This invention provides the ability to construct a portable x-ray fluorescence spectrometer capable of measuring low concentrations of randomly distributed analyte with x-ray energies greater than 15 KeV.

One application of the invention is a system for measuring the concentration of lead in dust wipe samples. In preferred embodiments the system includes a sensor assembly comprising a source of Co57 and associated collimators and depleted uranium fluorescent element for producing a beam of gamma and x-ray radiation such that a band across the width of the sample is uniformly irradiated, a detector equal in length to the source of radiation capable of uniformly detecting x-rays emitted from the sample, a sample holder fabricated from mylar and attached to a drive mechanism capable of advancing the sample in a direction perpendicular to the axis of the source/detector assembly and capable of real time regulation of sample scan speed, a transmitted radiation trap designed to suppress unwanted backscatter contributions to the signal, an amplifier capable of converting charge fluctuations across the detector contacts into voltage pulses, window comparators configured to pass pulses within fixed voltage ranges, a data acquisition module to count pulses from the window comparators and a computer to run the program that processes the counts stored in the counters of the data acquisition module. The computer also regulates the acquisition time and scan increment of the sample, provides the user interface and data storage capability for the device.

DESCRIPTION OF PREFERRED EMBODIMENTS OF THE INVENTION

STRUCTURE

Figure 1:
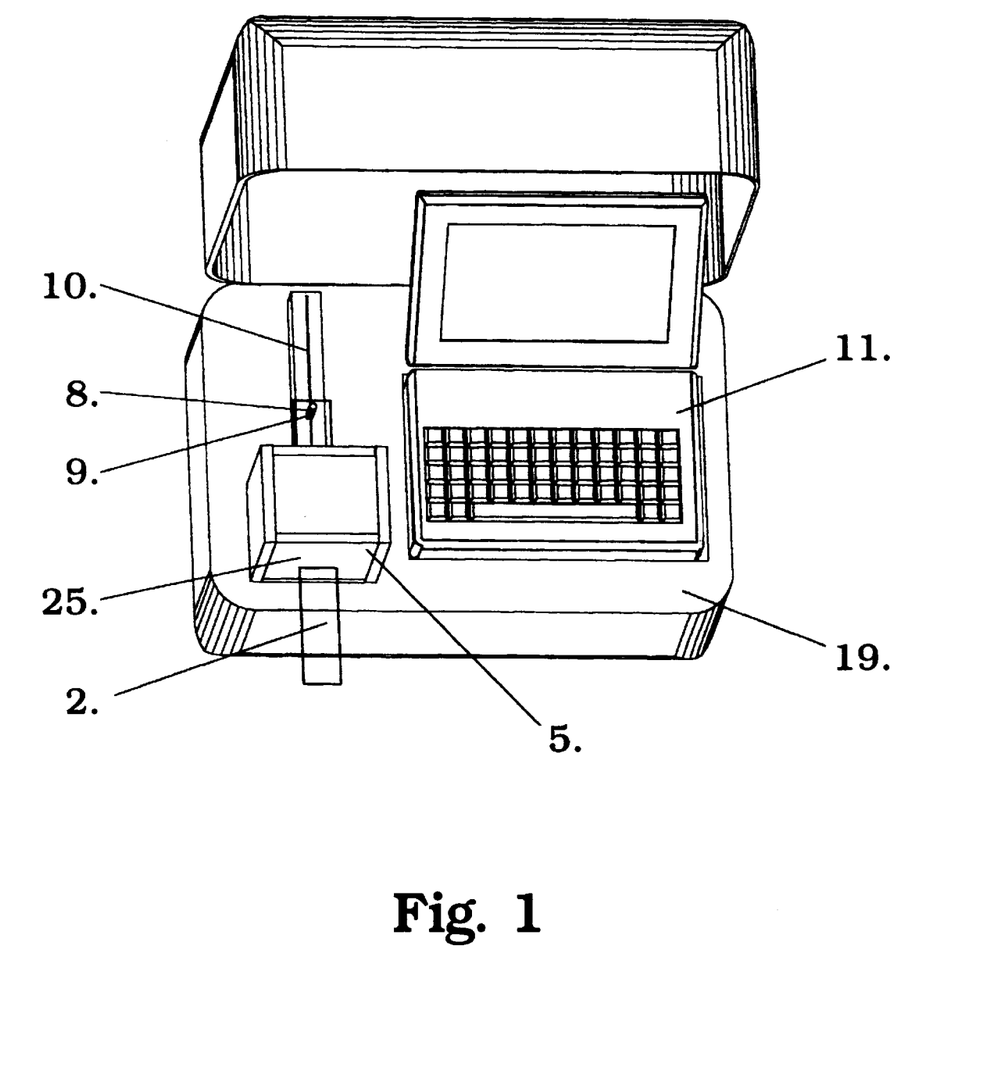
FIG. 1 is a perspective view of the portable lead dust wipe analyzer system.

Referring to FIG. 1, a compact and portable x-ray fluorescence lead dust wipe analyzer is contained in a case 19 with a handle (not shown) for convenient transportation. The case 19 encloses a computer 11 which is programed to control mechanical functions of the analyzer and convert nuclear counts from a detector (not shown) into a weight measurement of the analyte being measured. The XRF analyzer includes a radiation shield 5 which protects the operator from x-rays and other emissions from the enclosed radiation source and detector units that will be described in more detail below. The radiation shield includes a slot 25 through which a sample holder 2 made from low density material, for example mylar, travels between a pair of edge guides (not shown) by means of a motor I 0 driven engagement pin 9 under control of the computer 11. The pin 9 engages a hole 8 in the sample holder 2.

Figure 2:
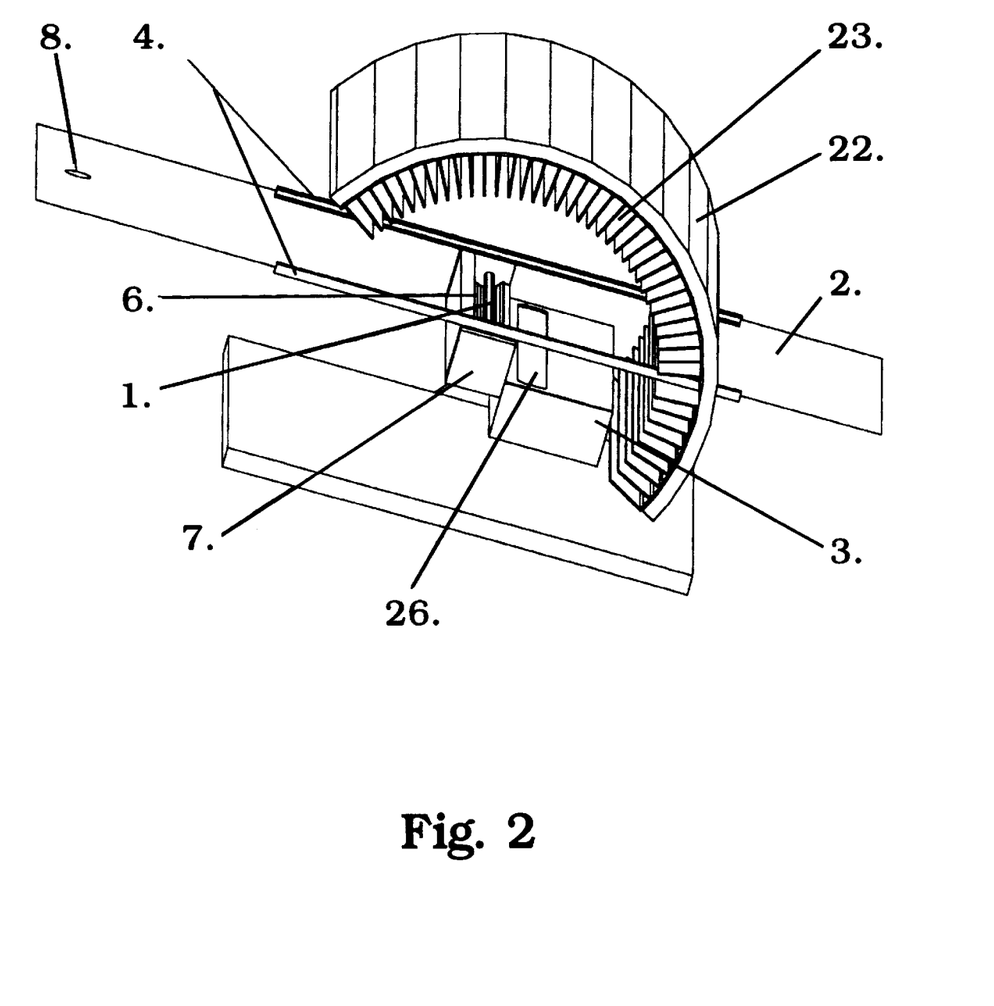
FIG. 2 shows a perspective view of the source assembly, detector assembly, sample holder and transmitted radiation trap with the shielding removed.
Figure 3:
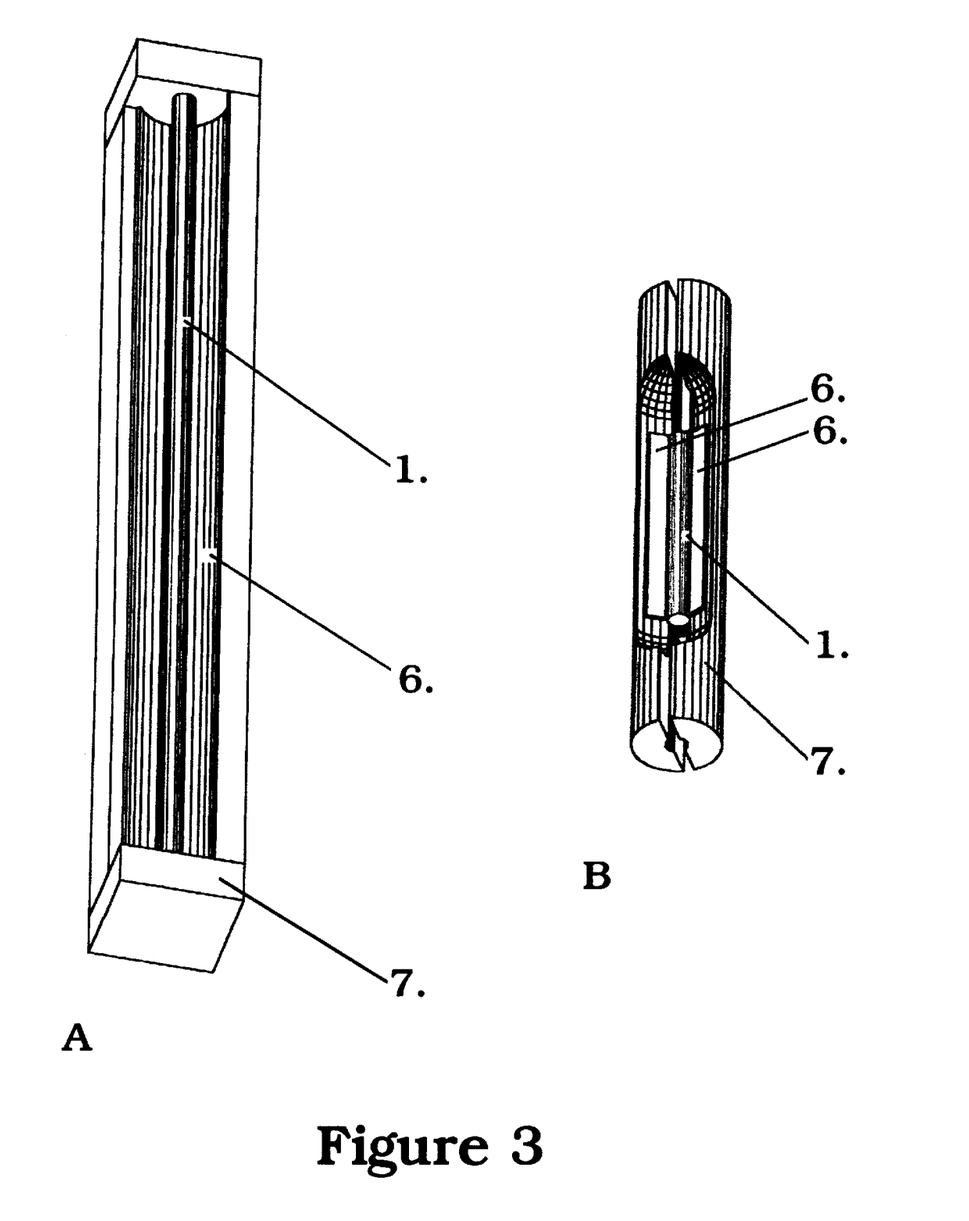
FIGS. 3a and 3b are perspective views of two enhanced source assemblies.

Referring to FIG. 2, the sensor assembly, shown in perspective view with the shielding removed, includes a source of radiation 1, having a generally linear shape that extends across the entire width of the sample holder 2, and a generally linear detector 3, with a thin aluminum window 26 positioned over the active area of the detector crystals, extending similarly across the width of the sample holder 2 and in a parallel relationship with respect to the source 1. Guide rails 4 control the path of the sample holder 2. The detector assembly 3 is mounted beside the source assembly 1,6,7. The source/detector assembly is mounted in an enclosure 5 fabricated from sintered tungsten (see FIGS. 1–5). The enclosure surrounds a radiation trap composed of a radial array of tin plates 23. The array is mounted on a 180 degree section of aluminum tubing 22. The entire trap assembly is mounted such that its axis is the line source 1. In the preferred embodiment, a 1 mm tin layer covers all sintered tungsten surfaces exposed to the detector. A sample position sensor comprising an led 41 and a photodiode 42 detects the leading edge of the sample. As discussed in more detail below, the orientation and linear geometry of the source and detector, along with controlled data acquisition, provides simple and reliable quantitative measurement of small quantities of lead irregularly distributed on samples such as post abatement dust wipes.

In FIG. 3A, the source assembly includes a one inch source and uranium enhancement elements fabricated from bars of the metal, mounted in the source holder. Referring as well to FIG. 3B, the source 1 is a five inch Co57 line source positioned in a holder 7 made by machining a concave depression in a one inch diameter bar of high density material, for example sintered tungsten. The depression in the rod is lined with a thin layer of depleted uranium 6. Co57 emits gamma rays with a predominant peak at 122 KeV. Although these gamma rays will cause lead to fluoresce, radiation that has an energy just slightly higher than the absorption edge of the element under investigation is the most efficient energy for causing fluorescence. Uranium has a gamma energy of 94.6 KeV which is slightly higher than the K absorption edge of lead at 87.95 KeV. The 122 KeV gamma rays emitted by Co57 cause uranium to fluoresce, and in turn the x-rays emitted by the uranium elements are efficient in generating lead fluorescence. Photons from the source assembly irradiate the sample in the sampleholder 2 with a combination of Co57 gamma rays and fluorescent x-rays emitted by the depleted uranium. The combination of the uranium x-rays with the primary source of Co57 gamma radiation provides a significant increase in lead fluorescence in comparison to Co57 alone.

Figure 4:
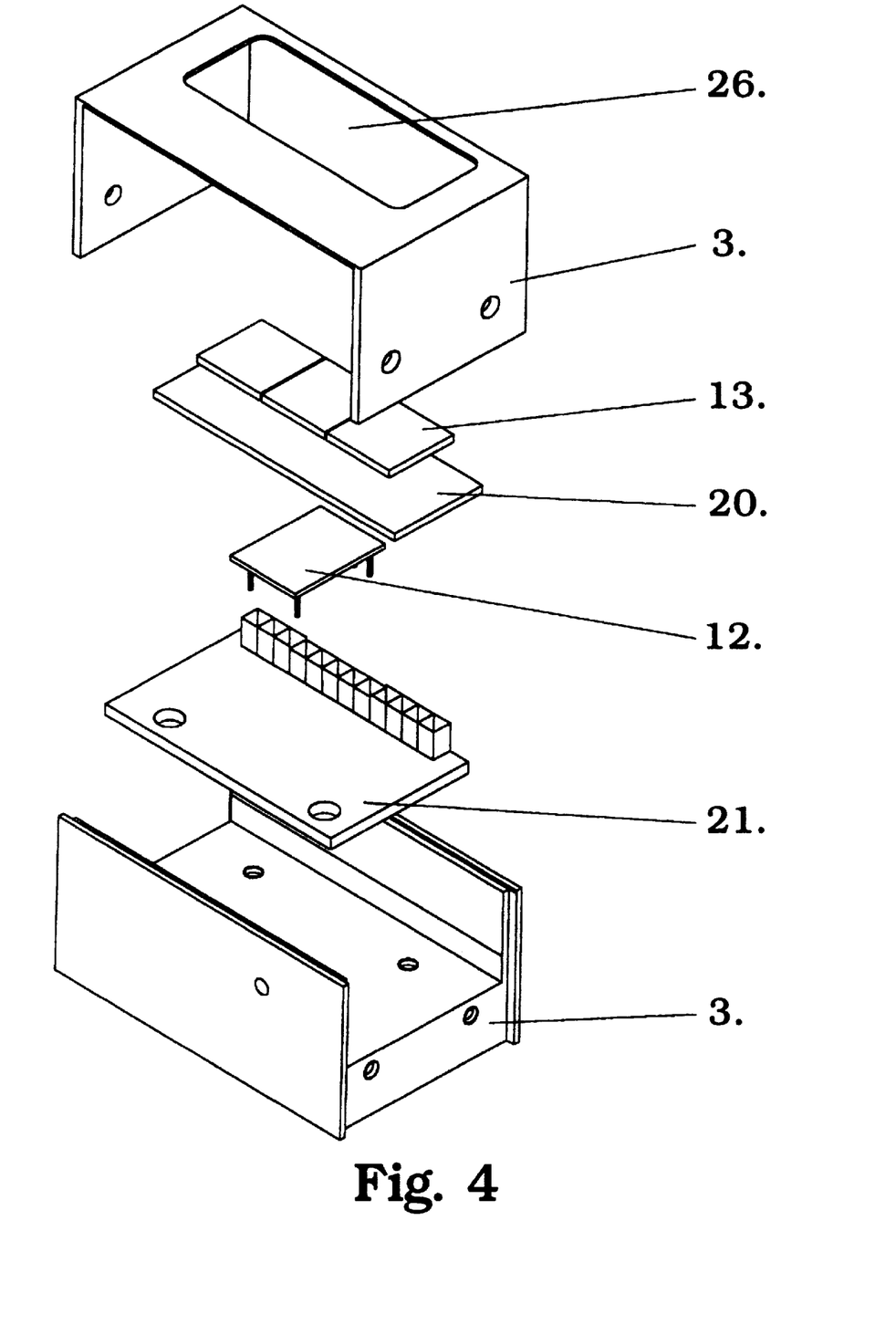
FIG. 4 is an exploded view of the detector.

Referring to FIG. 4, the detector unit includes an aluminum housing 3 with a thin aluminum window 26 (less than 0.001 inch) which contains an array of cadmium zinc telluride crystals 13 with ohmic contacts covering their major faces. The crystals 13, are mounted on a ceramic substrate 20. The crystals are rectangular in shape and arranged side-by-side to form a bar that is equal in length to the source. The CZT crystals have good energy resolution (8 KeV@60 KeV) and can operate at room temperature. The substrate also includes pins which connect to a preamplifier board 12 (eV Products, Saxonburg Pa. Model #5127). The preamplifier board also includes connections for detector bias voltage (Not shown). Pins extending from the preamplifiers engage connectors on a PCB 21 which is attached to the housing 3. A high voltage power supply (not shown) provides bias voltage to the detector crystals via a BNC cable.

Circuit Description

Figure 5:
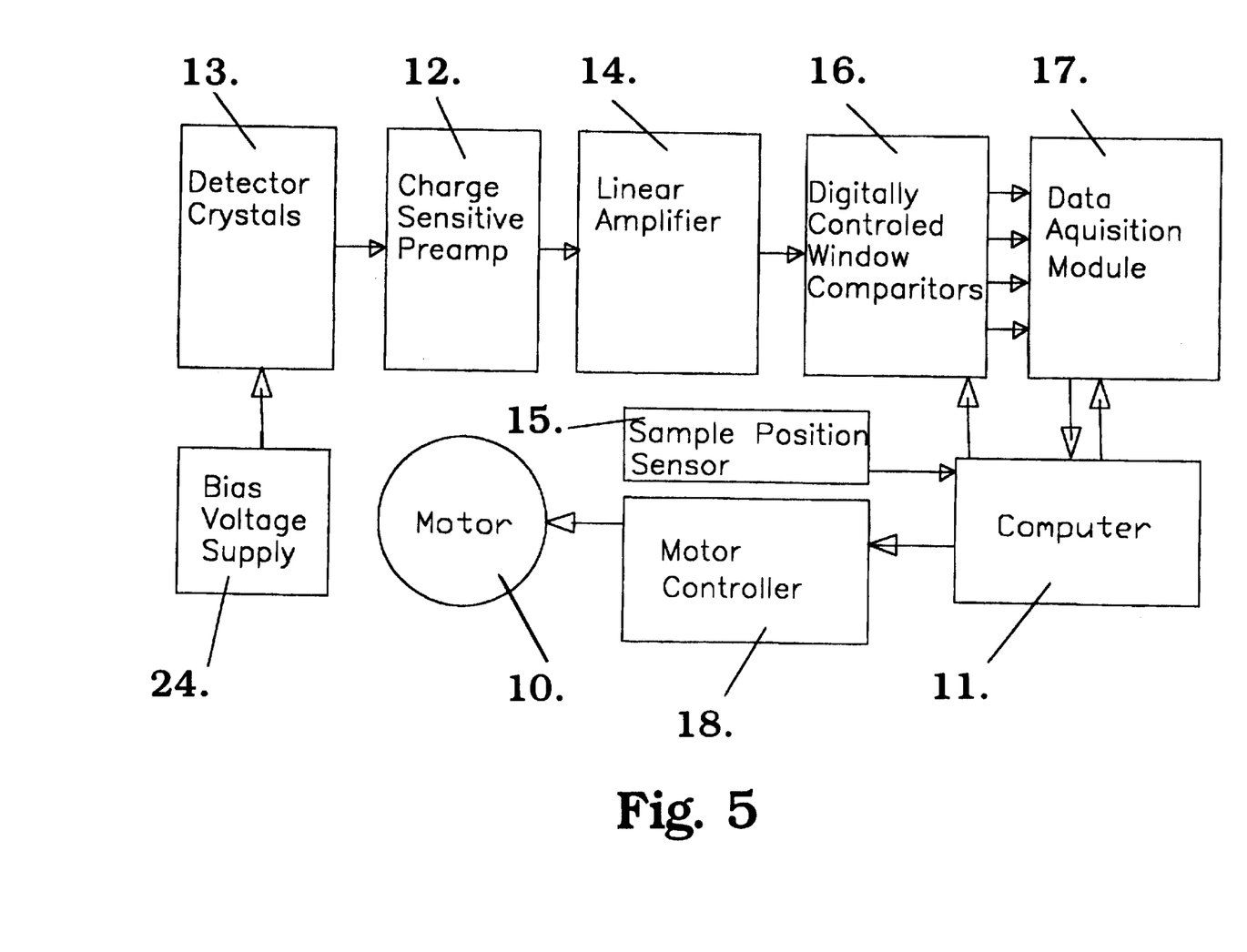
FIG. 5 is a functional block diagram illustrating the electronic circuitry of the device.

Referring to FIG. 5, the CZT crystals 13 are connected to the input of a charge sensitive preamplifier 12. A high voltage power supply 24 provides 200 volts of direct current which is applied across the CZT crystals to provide detector bias voltage. A cable (not shown) connects the preamplifier 12, to an additional amplifier stage comprising a linear amplifier 14. The linear amplifier 14 differentiates and integrates the incoming preamplifier signal resulting in an output of voltage pulses with a time constant of 1 microsecond. The linear amplifier 14 output is connected to the input of a bank of digitally controlled window comparators 16 the use of which is explained below. TTL level pulses are output by the window comparators when an input pulse has a voltage value which falls between the comparators upper and lower settings. These four channels of pulses are counted and stored by the data acquisition module 17. The computer 11 reads the values stored in the data acquisition module's counters and clears them at the end of each measurement cycle, under program control.

Referring also to FIG. 5, the sample holder 2 shown in FIG,. 2 is advanced across the sensor assembly by means of a stepper motor 10 controlled by the computer 11 by means of a motor controller card 18 (Hurst Princeton, Ind. model EPC-013).

Figure 6:
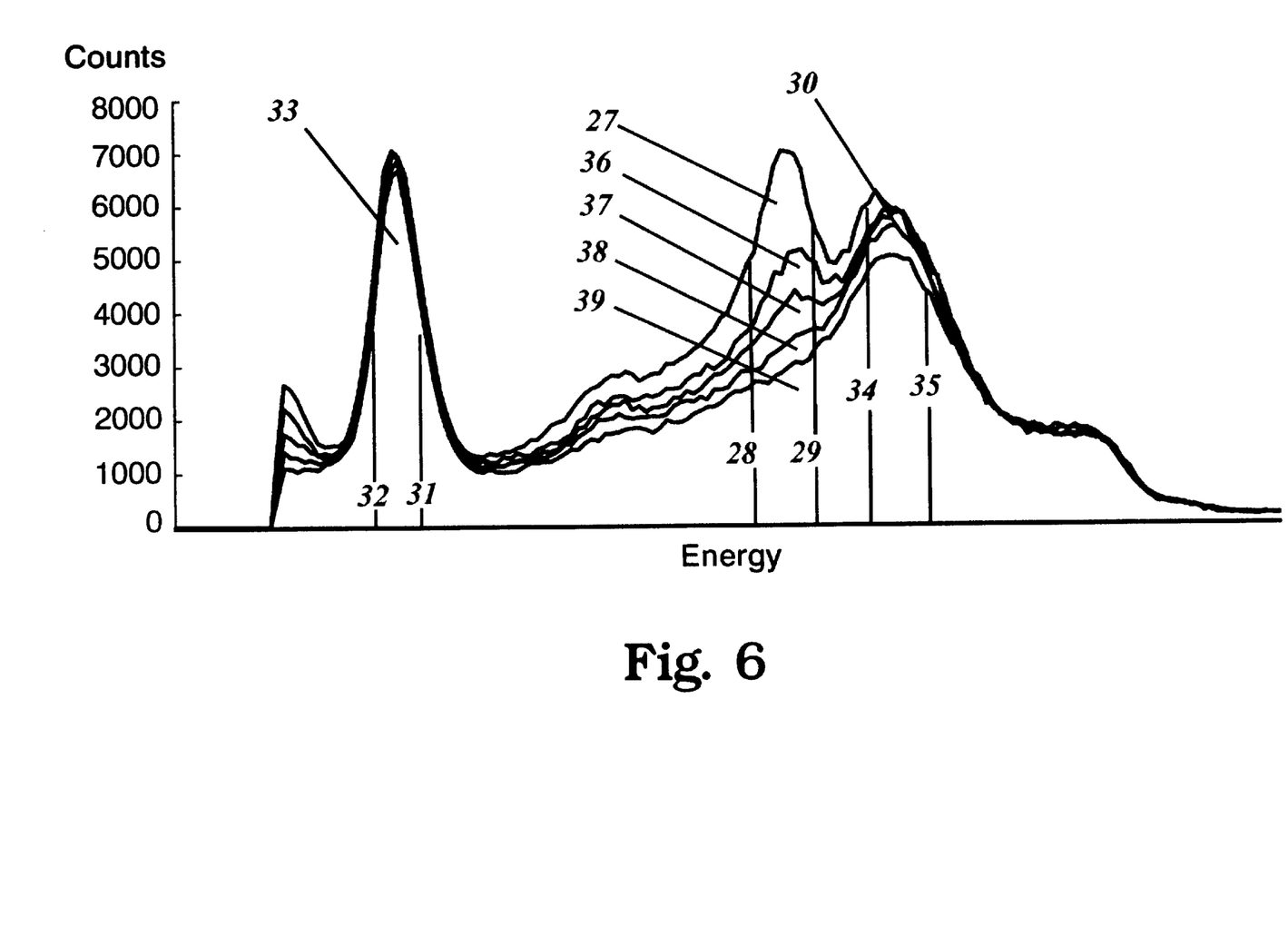
FIG. 6 displays representative spectra from the device.

Referring to FIG. 6, the upper and lower levels of two of the windows of the digitally controlled comparators are set to the electrical equivalent of the FWHM (Full Width Half Maximum) of the analyte peak 27. One window 28-29 is centered on the analyte peak 27, and the other window 34-35 is centered on the backscatter peak 30. Two additional windows are set to the electrical equivalent of 2 KeV. The windows are centered on the upper half maximum 31 and lower half maximum 32 of the tin peak 33. The pair of windows at the upper and lower half maximum of the tin peak are used to monitor system amplitude by measuring the consistency of their ratio. A shift in the ratio signals a change in amplitude. The position of the bank of windows is adjusted under program control to compensate for the monitored gain shift.

Process

Figure 7:
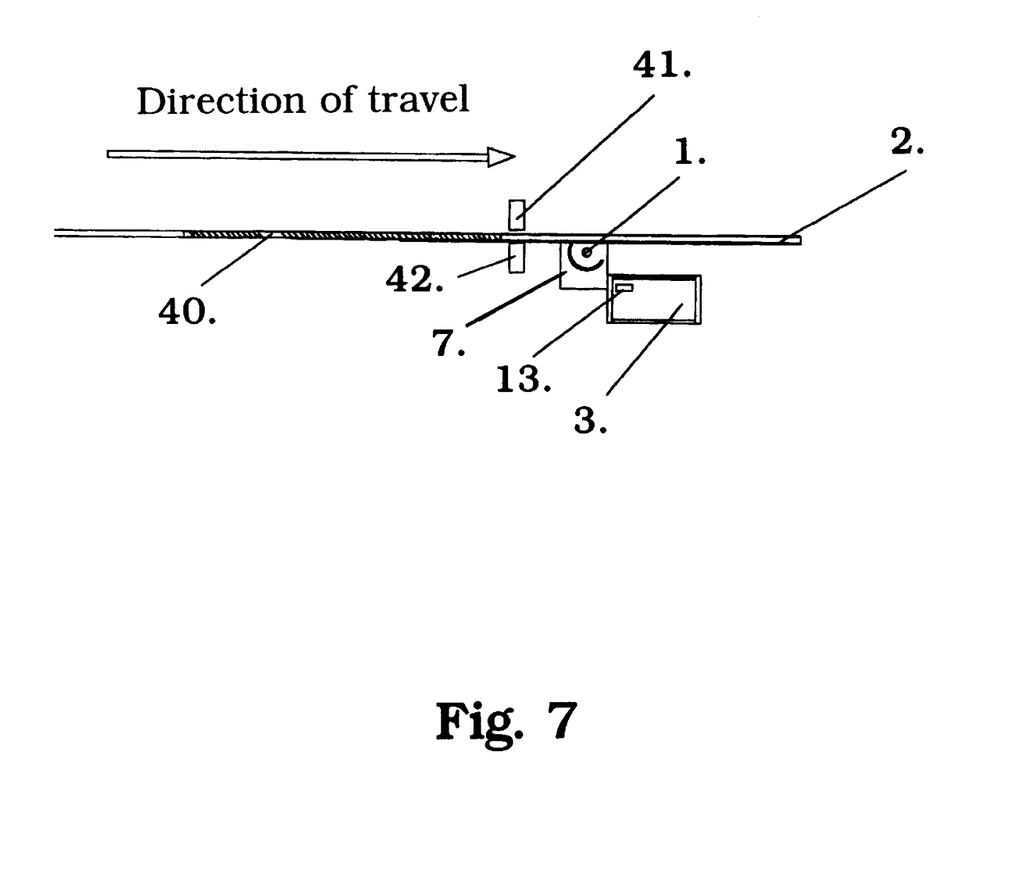
FIG. 7 displays a schematic representation of the key components of the sensor assembly.

Referring to FIG. 7, Sample 40 position is sensed by a sample position sensor 41,42 comprised of an LED 41 and a photo diode 42. At the beginning of the measurement cycle, the sample holder 2 is advanced until the leading edge of the sample 40 breaks the beam of the sample position sensor. Once the sample's position is determined, the sample is indexed to the start position and measurement commences. When the tail end of the sample 40 passes beyond the sample position sensor 41,42 the beam is re-established signaling, the program to begin a countdown of the cycles remaining until the test is complete.

Control over the magnitude of the accumulating backscatter contribution to the signal must be accomplished to achieve a reasonable level of accuracy. If data is collected until the entire mylar holder 2 and sample 40 has passed over the sensor assembly, the process exposes the entire sample to a uniform radiation flux and measurement time. However, the background will accumulate during the several minutes of testing and impose a huge background to signal ratio. This problem is reduced by breaking the scan into a series of shorter observations. The distance the sample is advanced between measurements is 2 mm. The width of the useful field of view of the detector is approximately 14 mm. In the preferred embodiment the sample is indexed 2 mm to allow all points on the sample to be exposed to the same gradient of radiation flux over time as each point on the sample will be measured at seven positions while it passes through the detectors field of view.

Counts from the system produce a multichannel analyzer spectrum similar to that in FIG. 6. The backscatter or zero analyte spectrum 39, exhibits a wide peak, and a shoulder that extends from the low energy side of that peak, a slope that diminishes with decreasing energy down to a tin x-ray peak 33. Because of this backscatter spectrum, a significant number of background events lie under the K x-ray peaks of the analyte. Analyte concentrations of 1000 micrograms 27, 500 micrograms 36, 250 micrograms 37, 75 micrograms 38 and 0 micrograms 39 are shown. The shape of the backscatter spectrum is fixed in that it arises from the sampleholder, collection medium and mechanical components which surround the source and detector.

Referring again to FIG. 6, to perform an analysis, the analyzer records events in the two regions of interest (ROI) which encompasses the analyte peak 28-29 and the backscatter peak 34-35. The backscatter signal must be removed from the analyte region of the spectrum before accurate determination of the lead concentration can be made. The ratio of the counts in the two windows is constant for a constant analyte concentration being a manifestation of the physical structure of the device, sample and to an extent the concentration of analyte contained in the sample. It can be observed that the amplitude of the backscatter peak 30 is modulated by varying analyte concentration. It has been determined experimentally that this modulation is backscatter from the analyte, and its effect on signal is linear with respect to analyte concentration. Because the effect is linear, it does not change the ratio of the two regions of the spectrum and can be ignored. Let the counts contained in ROI 28-29=A and the counts in ROI 34-35=B. The ratio A/B with no analyte present (RO) is used to estimate the backscatter's contribution to region A during a measurement by multiplying the counts in B by RO. This calculation yields the backscatter counts in A. This value is subtracted from A. The remainder is the analyte signal.

When data is moved into the computer program at the end of each observation, the data acquisition module counters are cleared. This retains the analyte data while removing the backscatter from the data thus improving the signal to background ratio. In the preferred embodiment the computer program estimates the lead counts by summing the measurement data acquired using:

Equation 1

$$Lead_{(counts)} = \sum_{i=1}^{n} (f(x))_1 + (f(x))_2 + \ldots (f(x))_n$$

Where:

$f(x) = A_i - (B_i R_s)$ $A_i$=the counts in the region encompassing the lead peak for the current observation.

$B_i$=the counts in the region encompassing the backscatter peak for the current observation.

$R_s$=the ratio of the backscatter counts in regions A and B at initial calibration.

The constant that represents the systems sensitivity as measured in counts per microgram of lead per unit time is defined as $cts_{pb}$. $Cts_{pb}$ is found at initial device calibration by dividing the lead concentration of a set of known samples by the number of lead counts recorded in a given time period. The acquisition time is set during initial device calibration such that the data collected in one observation has a 95% confidence level. That time ($T_i$) is expressed in seconds. Real time measurement of observations would allow the constant $cts_{pb}$ to fluctuate under the influence of source decay. The consistency of $cts_{pb}$ is maintained by dynamically controlling the measurement period of the observations as the inverse of the current source strength using the radioactive decay law as follows:

Equation 2

$$R_t = R_0 e^{-(0.693 \, t/t_{1/2})}$$

Where:

$R_t$=current source strength, $R_0$=initial source strength, t=elapsed time since initial calibration, $T_{1/2}$=half life of the source.

Then the current acquisition time is calculated as:

$T_c = T_i / R_t$

Where:

$T_i$=the acquisition time at initial calibration, $T_c$=the current acquisition time, $R_t$=current source strength.

At the completion of the scan, the lead total in micrograms is calculated by dividing the sum of the series of observations by the number of counts produced by a microgram of lead, which is expressed as $cts_{Pb}$. To express the answer in micrograms per square foot, $cts_{Pb}$ is divided by the sample area (a), measured in square feet. In the preferred embodiment the final lead concentration equation is:

Equation 3

$$Lead_{(\mu gm/ft.^2)} = \frac{1}{cts_{Pb} \, a} \sum_{i=1}^{n} (f(x))_1 + (f(x))_2 + \ldots (f(x))_n$$

Where:

$f(x) = A_i - (B_i R_s)$

SUMMARY OF OPERATION AND USE OF THE PREFERRED EMBODIMENT

In the field the operator plugs the unit into a 120-AC outlet and turns on the power switch. There is a pause during which the computer program is loaded into memory, the drive mechanism is positioned at its start position and current source strength is measured. Upon completion of these tasks the first menu is displayed on the computer screen. This menu displays the following options: 1. Enter site data, 2. Make a measurement, 3. Download test data, 4. Calibrate device. The operator is guided through the steps for each of these options by a series of sub-menus.

Upon selecting enter site data, the operator is presented with a form onto which information about the current test is entered. The sample is given an identification code that the operator transcribes onto the sampleholder, which is saved with the sample. A new sampleholder is used for each test. After completion of the form, the device offers two choices: return to main menu or perform a measurement.

Samples of dust are collected by standard protocol. For example, on floors a damp paper wipe is rubbed across a two square foot area in an "S" wise manner and then the paper wipe is folded and the process repeated at 90 degrees from the first pass. The wipe is then positioned between registration guides printed on the sample holder and the holder is slid into the sensor assembly. A hole at the end of the sample holder is fitted onto a pin that connects the sample holder to the drive mechanism. The operator then presses the start button to begin the measurement. At the end of the measurement cycle, the device prompts the operator that the test is completed. The operator removes the sampleholder with the sample.

To download data from the device, the operator connects the device to the computer that will receive the data with a standard RS232 cable. A program in the receiving computer prepares it to receive the data. When the receiver is ready, the operator selects the download data option. After successful transfer of data, the device prompts the operator that the process is complete and offers the option to clear the data memory.

Calibration of the spectrometer is accomplished through a series of measurements. A standard sample medium, be it paper or liquid that contains no analyte, is measured to determine its background and scatter spectrum and to quantify its contribution to the ROIs that encompass the analyte and backscatter peaks. The ratio of the counts in the two ROIs is constant for a given sample medium, and is used in equation 1 to strip the background and scatter counts that fall into the analyte ROI. In the second step of the calibration, standard samples with known concentrations of the analyte to be measured are loaded into the sampleholder and measured. The results of these measurements provide data that is used to define the systems sensitivity in terms of counts/microgram. In cases where the counts obtained are not linear with respect to analyte concentration, the difference between the actual concentration and the measured concentration is plotted and a regression analysis of the data is used to define the systematic error curve. The result is used to linearize the systems output.

OTHER EMBODIMENTS OF THE INVENTION

In other embodiments of the invention the sample holding apparatus is altered to accommodate analysis of filter media such as are found in an air sampling device to measure the concentration of lead or other elements. This embodiment would be useful in monitoring air quality during removal of lead based paint from structural steel. Air sampling is an excellent method for assessing air quality in industries like smelting or mining. Air sampling is also useful to monitor other industrial contaminants.

In other embodiments of the invention, the system is calibrated to measure other elements. The K shell x-rays of any element which produces x-rays with energies greater than 15 KeV can easily be detected using CZT detectors. A lookup table containing ROI position, cts/microgram of analyte, RC and correction factors for a variety of alloys can be compiled and stored to allow measurement of a variety of metals. For example, this technique would be useful for measurement of cadmium.

In another embodiment of the invention lead or other heavy elements in soil samples can be measured. The sample holder may consist of a rectangular dish fabricated from plastic or other low density waterproof material capable of holding the soil sample. In a related application, a core sample of soil is positioned in the sample holder. Rather than sum the successive measurements, each is recorded individually. The series of measurements reveals the concentration of analyte as a function of its position in the sample. This embodiment would be useful in characterizing the distribution of a variety of environmental poisons including mercury, cadmium and uranium. Other embodiments are included in the following claims.

What is claimed:

1. A device for measuring accurately the content of lead contained in a dust wipe sample, said device comprising a linear excitation source of Cobalt 57 in a holder, said holder consisting of a 4 inch long by 1 inch diameter sintered tungsten bar with a 0.3 inch slot positioned radially extending along said bar, said slot has a depth which produces a collimated beam of radiation the width of which is limited to the area of the sample within the field of view of the detector, a depleted uranium coating covering the surface of said slot, producing a beam of ionizing radiation capable of exciting the emission of primary x-rays by the lead contained in said wipe sample, said sample comprising a paper wipe containing the sample held in a sample holder comprising a folder of 0.005 inch thick mylar, said folders dimensions are 4 inches by 10 inches, said folder is folded on its 4 inch side, said sample held in said holder is mechanically drawn through said beam in a direction perpendicular to the axis of said source, a linear detector comprising an array of cadmium zinc telluride crystals 0.5 centimeters wide and 6 centimeters long, said detector is positioned on a plain parallel to said sample and positioned such that its sensitive area faces said sample at the point where said beam passes through said sample, a transmitted radiation trap composed of a radial array of tin plates, said array is positioned such that it shares the axis of said linear source of radiation, and is positioned such that said sample travels on a plain between said source and said radiation trap, an analyzer, and an indicator; said analyzer including an algorithm providing the capability of calculating current source strength to compensate for source decay through control of acquisition time, and making use of a further algorithm, capable of distinguishing between the x-ray emitted by lead from all others, said analyzer having the capability of providing an accurate reading of the concentration of lead in the sample.

2. A device for measuring accurately the content of lead contained in an air filter, said device comprising a linear excitation source of Cobalt 57 in a holder, said holder consisting of a 4 inch long by 1 inch diameter sintered tungsten bar with a 0.3 inch slot positioned radially extending along said bar, said slot has a depth which produces a collimated beam of radiation the width of which is limited to the area of the sample within the field of view of the detector, a depleted uranium coating covering the surface of said slot, producing a beam of ionizing radiation capable of exciting the emission of primary x-rays by the lead contained in said air filter, said sample comprising a paper wipe containing the sample held in a sample holder comprising a folder of 0.005 inch thick mylar, said folders dimensions are 4 inches by 10 inches, said folder is folded on its 4 inch side, said sample held in said holder is mechanically drawn through said beam in a direction perpendicular to the axis of said source, a linear detector comprising an array of cadmium zinc telluride crystals 0.5 centimeters wide and 3 centimeters long, said detector is positioned on a plain parallel to said sample and positioned such that its sensitive area faces said sample at the point where said beam passes through said sample, a transmitted radiation trap composed of a radial array of tin plates, said array is positioned such that it shares the axis of said linear source of radiation, and is positioned such that said sample travels on a plain between said source and said radiation trap, an analyzer, and an indicator; said analyzer including an algorithm providing the capability of calculating current source strength to compensate for source decay through control of acquisition time, and making use of a further algorithm, capable of distinguishing between the x-ray emitted by lead from all others, said analyzer having the capability of providing an accurate reading of the concentration of lead in the sample.

3. A device for measuring accurately the content of lead contained in a soil sample, said device comprising a linear excitation source of Cobalt 57 in a holder, said holder consisting of a 4 inch long by 1 inch diameter sintered tungsten bar with a 0.3 inch slot positioned radially extending along said bar, said slot has a depth which produces a collimated beam of radiation the width of which is limited to the area of the sample within the field of view of the detector, a depleted uranium coating covering the surface of said slot, producing a beam of ionizing radiation capable of exciting the emission of primary x-rays by the lead contained in said soil sample, said sample comprising said soil held a rectangular dish, said dish dimensions are 4 inches by 10 inches with a depth of 1 inch, said sample held in said holder is mechanically drawn through said beam in a direction perpendicular to the axis of said source, a linear detector comprising an array of cadmium zinc telluride crystals 0.5 centimeters wide and 3 centimeters long, said detector is positioned on a plain parallel to said sample and positioned such that its sensitive area faces said sample at the point where said beam passes through said sample, a transmitted radiation trap composed of a radial array of tin plates, said array is positioned such that it shares the axis of said linear source of radiation, and is positioned such that said sample travels on a plain between said source and said radiation trap, an analyzer, and an indicator; said analyzer including an algorithm providing the capability of calculating current source strength to compensate for source decay through control of acquisition time, and making use of a further algorithm, capable of distinguishing between the x-ray emitted by lead from all others, said analyzer having the capability of providing an accurate reading of the concentration of lead in the sample.

4. A device for measuring accurately the content of lead contained in a soil core sample, said device comprising a linear excitation source of Cobalt 57 in a holder, said holder consisting of a 4 inch long by 1 inch diameter sintered tungsten bar with a 0.3 inch slot positioned radially extending along said bar, said slot has a depth which is 1.25 times the radius of said bar, a depleted uranium coating covering the surface of said slot, producing a beam of ionizing radiation capable of exciting the emission of primary x-rays by the lead contained in said soil core sample, said sample comprising soil extracted from the ground by driving a 4 inch by 0.5 inch rectangular metal pipe into the ground, said soil is held a rectangular dish, said dish dimensions are 4 inches by the length of said core sample with depth of 1 inch, said sample held in said holder is mechanically drawn through said beam in a direction perpendicular to the axis of said source, a linear detector comprising an array of cadmium zinc telluride crystals 0.5 centimeters wide and 3 centimeters long, said detector is positioned on a plain parallel to said sample and positioned such that its sensitive area faces said sample at the point where said beam passes through said sample, a transmitted radiation trap composed of a radial array of tin plates, said array is positioned such that it shares the axis of said linear source of radiation, and is positioned such that said sample travels on a plain between said source and said radiation trap, an analyzer, and an indicator; said analyzer including an algorithm providing the capability of calculating current source strength to compensate for source decay through control of acquisition time, and making use of a further algorithm, capable of distinguishing between the x-ray emitted by lead from all others, said analyzer having the capability of providing an accurate reading of the concentration of lead as a function of its position along the axis of the sample.

5. A device for measuring accurately the content of lead contained in a dust wipe sample, said device comprising a linear excitation source of ionizing radiation with a length equal to or greater than the sample to be measured, in a holder, said holder consisting of a bar of high density material with a slot positioned radially extending along said bar, said slot has a depth which produces a collimated beam of radiation the width of which is limited to the area of the sample within the field of view of the detector, a depleted uranium coating covering the surface of said slot, producing a beam of ionizing radiation capable of exciting the emission of primary x-rays by the lead contained in said wipe sample, said sample comprising a paper wipe containing the sample held in a sample holder comprising a folder of 0.005 inch thick Mylar, said sample held in said holder is mechanically drawn through said beam in a direction perpendicular to the axis of said source, a linear detector of ionizing radiation, said detector is positioned on a plain parallel to said sample and positioned such that its sensitive area faces said sample at the point where said beam passes through said sample, a transmitted radiation trap composed of a radial array of tin plates, said array is positioned such that it shares the axis of said linear source of radiation, and is positioned such that said sample travels on a plain between said source and said radiation trap, a controller, an analyzer, and an indicator; said controller including an algorithm providing the capability of calculating current source strength to compensate for source decay through control of acquisition time, said analyzer, capable of distinguishing between the x-ray emitted by lead from all others, said analyzer having the capability of providing an accurate reading of the concentration of lead in the sample.

6. A device for measuring accurately the content of lead contained in an air filter, said device comprising a linear excitation source of ionizing radiation with a length equal to or greater than the sample to be measured, in a holder, said holder consisting of a bar of high density material with a slot positioned radially extending along said bar, said slot has a depth which produces a collimated beam of radiation the width of which is limited to the area of the sample within the field of view of the detector, a depleted uranium coating covering the surface of said slot, producing a beam of ionizing radiation capable of exciting the emission of primary x-rays by the lead contained in said air filter sample, said sample comprising a paper or other filter medium containing the sample, said sample mechanically drawn through said beam in a direction perpendicular to the axis of said source, a linear detector of ionizing radiation, said detector is positioned on a plain parallel to said sample and positioned such that its sensitive area faces said sample at the point where said beam passes through said sample, a transmitted radiation trap composed of a radial array of tin plates, said array is positioned such that it shares the axis of said linear source of radiation, and is positioned such that said sample travels on a plain between said source and said radiation trap, a controller, an analyzer, and an indicator; said controller including an algorithm providing the capability of calculating current source strength to compensate for source decay through control of acquisition time, said analyzer making use of an algorithm, capable of distinguishing between the x-ray emitted by lead from all others, said analyzer having the capability of providing an accurate reading of the concentration of lead in the sample.

7. A device for measuring accurately the content of lead contained in a soil sample, said device comprising a linear excitation source of ionizing radiation with a length equal to or greater than the sample to be measured, in a holder, said holder consisting of a bar of high density material with a slot positioned radially extending along said bar, said slot has a depth which produces a collimated beam of radiation the width of which is limited to the area of the sample within the field of view of the detector, a depleted uranium coating covering the surface of said slot, producing a beam of ionizing radiation capable of exciting the emission of primary x-rays by the lead contained in said soil sample, said sample comprising soil held a rectangular dish, said sample held in said holder is mechanically drawn through said beam in a direction perpendicular to the axis of said source, a linear detector of ionizing radiation, said detector is positioned on a plain parallel to said sample and positioned such that its sensitive area faces said sample at the point where said beam passes through said sample, a transmitted radiation trap composed of a radial array of tin plates, said array is positioned such that it shares the axis of said linear source of radiation, and is positioned such that said sample travels on a plain between said source and said radiation trap, a controller, an analyzer and an indicator; said controller including an algorithm providing the capability of calculating current source strength to compensate for source decay through control of acquisition time, said analyzer making use of an algorithm, capable of distinguishing between the x-ray emitted by lead from all others, said analyzer having the capability of providing an accurate reading of the concentration of lead in the sample.

8. A device for measuring accurately the content of lead contained in a soil core sample, said device comprising a linear excitation source of ionizing radiation with a length equal to or greater than the sample to be measured, in a holder, said holder consisting of a bar of high density material with a slot positioned radially extending along said bar, said slot has a depth which produces a collimated beam of radiation the width of which is limited to the area of the sample within the field of view of the detector, a depleted uranium coating covering the surface of said slot, producing a beam of ionizing radiation capable of exciting the emission of primary x-rays by the lead contained in said soil sample, said sample comprising soil extracted from the ground by driving rectangular metal pipe into the ground, said soil is held a rectangular dish, said dish dimensions are similar to the pipe used to extract the sample, said sample held in said holder is mechanically drawn through said beam in a direction perpendicular to the axis of said source, a linear detector of ionizing radiation, said detector is positioned on a plain parallel to said sample and positioned such that its sensitive area faces said sample at the point where said beam passes through said sample, a transmitted radiation trap composed of a radial array of tin plates, said array is positioned such that it shares the axis of said linear source of radiation, and is positioned such that said sample travels on a plain between said source and said radiation trap, a controller, an analyzer and an indicator; said controller including an algorithm providing the capability of calculating current source strength to compensate for source decay through control of acquisition time, said analyzer making use of an algorithm, capable of distinguishing between the x-ray emitted by lead from all others, said analyzer having the capability of providing an accurate reading of the concentration of lead in the sample as a function of its position along the axis of the sample.

\* \* \* \* \*